US009129595B2

United States Patent
Russell et al.

(10) Patent No.: US 9,129,595 B2
(45) Date of Patent: Sep. 8, 2015

(54) ARTIFICIAL LARYNX

(75) Inventors: Megan Jill Russell, Johannesburg (ZA);
David Milton Rubin, Johannesburg (ZA); Brian Wigdorowitz, Johannesburg (ZA); Tshilidzi Marwala, Johannesburg (ZA)

(73) Assignee: UNIVERSITY OF THE WITWATERSRAND, Johannesburg (ZA)

( * ) Notice: Subject to any disclaimer, the term of this patent is extended or adjusted under 35 U.S.C. 154(b) by 754 days.

(21) Appl. No.: 13/003,114

(22) PCT Filed: Jun. 30, 2009

(86) PCT No.: PCT/IB2009/006125
§ 371 (c)(1),
(2), (4) Date: Apr. 26, 2011

(87) PCT Pub. No.: WO2010/004397
PCT Pub. Date: Jan. 14, 2010

(65) Prior Publication Data
US 2011/0190881 A1   Aug. 4, 2011

(30) Foreign Application Priority Data
Jul. 1, 2008   (ZA) .................................. 2008/05078

(51) Int. Cl.
*A61F 2/20*   (2006.01)
*A61B 5/103*   (2006.01)
*G10L 21/06*   (2013.01)
(Continued)

(52) U.S. Cl.
CPC . *G10L 13/02* (2013.01); *A61F 2/20* (2013.01); *A61F 2002/206* (2013.01); *G10L 2021/0575* (2013.01)

(58) Field of Classification Search
USPC ........... 623/9; 704/258–271, E21.02; 600/23, 600/586–593; 367/198
See application file for complete search history.

(56) References Cited

U.S. PATENT DOCUMENTS 5,326,349 A * 7/1994 Baraff ................................ 623/9
6,006,175 A * 12/1999 Holzrichter .................... 704/208
6,598,006 B1 * 7/2003 Honda et al. .................. 702/116
(Continued)

OTHER PUBLICATIONS

Takahashi, Hirokazu et al. "Alaryngeal Speech Aid Using an Intra-Oral Electrolarynx and a Miniature Fingertip Switch", Auris Nasus Larynx International Journal of ORI & HNS, Jan. 6, 2005, pp. 157-162, also available at www.elsevier.com/locate/anl.
(Continued)

*Primary Examiner* — Yashita Sharma
(74) *Attorney, Agent, or Firm* — Kevin R Erdman; Brannon Sowers & Cracraft PC

(57) ABSTRACT

This invention relates to a means for compensating for a whole or partial loss of speech. The means has a sensor unit in the form of a Logometrix pseudo palate and a palatometer which sense the position of a user's tongue while endeavouring to articulate words or sounds. The sensor unit is connected to a comparator which makes use of suitable artificial intelligence algorithms (such as Multi-Layer Perceptron Neural Networks and Hidden Markov Models) together with a library of stored words and sounds as well as tongue positions and signals related to jaw and lip movement as well as inhalation and exhalation to match words or sounds and transmit the matched words or sounds to a loudspeaker. Preferably the output of the loudspeaker will simulate the natural voice of the user.

18 Claims, 4 Drawing Sheets

Figure 1:
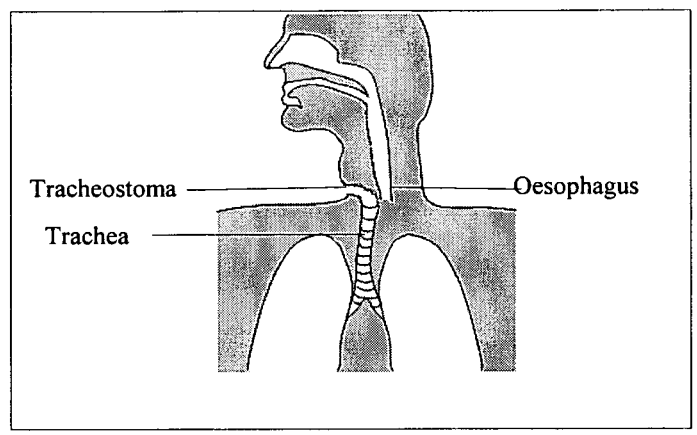

(51) Int. Cl.
*G10L 13/02* (2013.01)
*G10L 21/057* (2013.01)

(56) References Cited

U.S. PATENT DOCUMENTS 6,971,993 B2 * 12/2005 Fletcher .................. 600/587
2002/0087322 A1 * 7/2002 Fletcher .................. 704/270

OTHER PUBLICATIONS

Duxans, Helenca et al., "Voice Conversion of Non-Aligned Data Using Unit Selection", TC-Star Workshop on Speech-to-Speech Translation, Barcelona, Spain Jun. 2009, pp. 237 to 242.
Erro Daniel et al., "Frame Alignment Method for Cross-Lingual Voice Conversion", Department of Signal Theory and Communications, Universitat Politécnica de Catalunya (UPC), Barcelona, Spain, InterSpeech 2007—EuroSpeech. Antwerp, Belgium. Aug. 2007, 4 pages.
Erro Daniel et al., "Weighted Frequency Warping for Voice Conversion" Department of Signal Theory and Communications, Universitat Politécnica de Catalunya (UPC), Barcelona, Spain, InterSpeech 2007—4 pages.
Jassar, P et al. "Restoration of voice after laryngectomy", Journal of the Royal Society of Medicine, vol. 92, Jun. 1999, pp. 299-302.
Lim Marilyn et al., "Vowel Effect on Glottal Parameters and the Magnitude of Jaw Opening", Journal of Voice, vol. 20, No. 1, 2006, pp. 46-54.
Liu Hanjun et al., "Electrolarynx in voice rehabilitation", Auris Nasus Larynx, 34, 2007, pp. 327-332.
Menezes, C. et al., "Contrastive Emphasis: Comparison of Pitch Accents with Syllable Magnitudes", Department of Speech and Hearing Sciences, 4 pages.
Ng Manwa L. et al., "Speech Performance of Adult Cantonese-Speaking Laryngectomees Using Different Types of Alaryngeal Phonation", Journal of Voice, vol. 11, No. 3, 1997, pp. 338-344.
Ooe, Katsutoshi et al., "A New Type of Artificial Larynx Using a PZT Ceramics Vibrator as a Sound Source", IEEE/ASME Transactions on Mechatronics, vol. 5, No. 2, Jun. 2000, pp. 221-225.
Op de Coul B.M.R., et al., "A Decade of Postlaryngectomy Vocal Rehabilitation in 318 Patients. A Single Institution's Experience With Consistent Application of Provox Indwelling Voice Prostheses." Arch Otolaryngol Head Neck Surg, 126, 2000, pp. 1320-1328.
Russell, Megan et al., "Pattern Recognition and Feature Selection for the Development of a New Artificial Larynx", Proceedings of the World Congress of Biomedical Engineering and Medical, 2009, pp. 736-739.
Russell, M.J. et al., "The Artificial Larynx: A Review of Current Technology and a Proposal for Future Development", NBC 2008, Proceedings vol. 20, Jun. 2008, pages pp. 160-163.
Conley, John J. et al. "Panel Discussion: Rehabilitation of the Post-Laryngectomized Patient", Amer. laryngol. Assoc. pp. 2101-2107.
International Search Report for Application No. PCT/IB2009/006125 (2 pgs).
Russell, Rubin, Widgorowitz and Marwala, "The Artificial Larynx: A Review of Current Technology and a Proposal for Future Development", NBC, Jun. 16, 2008, pp. 160-163, also available at www.springerlink.com/content/u2840622hh7852q4. (4 pgs.).
Shoureshi et al., "Neural-Based Prosthesis for Enhanced Voice Intelligibility in Laryngectomees", IEEE Conference on Natural Engineering, Mar. 20, 2003, pp. 173-176, (4 pgs.).
Fagan, M.J. et al., "Development of a (silent) speech recognition system for patients following laryngectomy," Medical Engineering & Physics, Butterworth-Heinemann, May 1, 2008, pp. 419-425, (7 pgs.).

* cited by examiner

ARTIFICIAL LARYNX

CROSS-REFERENCE TO RELATED APPLICATION

This application is the National Stage filing of International Application Serial No. PCT/IB2009/006125, filed Jun. 20, 2009 and designating the United States, which claims priority to South African Application Serial No. 2008/05078, Filed Jul. 1, 2008, the entire disclosures of which are expressly incorporated by reference.

FIELD OF THE INVENTION

This invention relates to a means for compensating for the whole or a partial loss of speech following a a surgical procedure, for example, a laryngectomy, an accident or a congenital birth defect.

BACKGROUND TO THE INVENTION

The ability to communicate vocally is a skill many people take for granted. However, some people lose their ability to talk due to a surgical procedure like a laryngectomy. A laryngectomy is an operation in which the larynx (or "voice box") is removed from a patient due to laryngeal, oesophageal or pharyngeal cancer [1]. A number of alternatives are available to the patient to give them a means to communicate, however, as indicated below, none of these devices produce natural sounding speech.

Anatomically, the larynx is part of the conducting tube that joins the pharynx and the trachea. It has two main functions [2]:
1. to prevent food or drink from entering the trachea and lungs during swallowing; and
2. to produce sound.

It is made up of a number of different cartilages and muscles which hold the larynx open during breathing and which close the laryngeal opening (glottis) during swallowing and in speech. The epiglottis is a spoon-shaped structure that aids in closing the glottis during swallowing. The vocal folds in the larynx are controlled by muscles and are used in sound production [2].

A laryngectomy is a procedure used to remove the larynx. In a laryngectomy, the entire larynx including the thyroid and cricoids cartilages is removed [3]. Once this has been done the upper part of the trachea is attached to the front of the neck to create a permanent opening (the tracheostoma) [4]. This is illustrated in FIG. 1. The tracheostoma is mainly for breathing purposes. The laryngectomy results in the patient being totally unable to phonate and this is due to the complete removal of the vocal cords.

Current Options for Phonation

As indicated above, there are a number of ways in which a patient can attempt to regain his/her voice. However, Oesophageal and Tracheoesophageal speech are the most common with Tracheoesophageal speech fast becoming considered as the gold-standard in artificial speech production. Some of the common ways are:
1. Electrolaryngeal Speech: This involves the use of an electrolarynx, which is a battery-powered transducer that directs a buzzing noise into the patient's vocal tract [1]. The sound can be introduced via the neck using a handheld device or into the oral cavity using an intra-oral device. Patients then articulate the sound into words using their mouth. Pitch-controllable and volume-controllable devices are available [4].This form of rehabilitation has a short learning time and the ability to use the device immediately after the operation. It is also readily available and has a low-cost. However, this device produces a mechanical sound and is dependent on batteries and maintenance of the intraoral tubes [5].
2. Pneumatic Artificial Laryngeal Speech: This device is coupled to the tracheostoma on the patient's neck. When the patient wants to talk, air from the lungs is sent into the device which causes a rubber reed to vibrate and produce sound. This sound is then directed into the patient's mouth via a plastic tube for modulation [4]. This device has a short learning time and is low-cost but it produces a reedy sound and is conspicuous. It also requires maintenance of the intraoral tubes. This method is generally seen as obsolete.
3. Oesophageal Speech: This type of phonation requires no external device. The upper part of the patient's oesophagus serves as an air reservoir. When the patient wishes to communicate, this air is ejected from the oesophagus causing the pharyngoesophageal segment to vibrate, thus producing sound which the patient can modulate using their mouth [4]. This form of artificial speech is less conspicuous than the electrolarynx. It also requires no batteries, is not mechanical sounding, and is not manual. There is a large variation in the success rate of this method (14-76% reported success rates [6]) with some users abandoning the technique due to heartburn and bloating from the swallowed air [7].
4. Tracheoesophageal Speech: This is currently the most popular restorative option. A hole during (primary oesophageal puncture) or after (secondary oesophageal puncture) the laryngectomy operation is created between the trachea and the oesophagus. A unidirectional valve is then fitted into the hole that allows air to enter the oesophagus from the trachea. When the patient wants to phonate, the tracheostoma is blocked and air travels from the trachea into the oesophagus. This causes vibration and a source of sound that the patient can modulate [4].This method has a good success rate (95% of patients achieve effective conversational speech with 88% achieving good voice quality [8]). This method requires manual covering of stoma during speech and regular maintenance and replacement of the prosthesis.

Despite the different options above, a significant percentage, 7-40%, of patients never regain any form of speech [1].

A number of novel artificial larynxes have been proposed in recent literature. Research is being done into a new vibration source for Electrolarynxs by [9] using PZT ceramics. By studying the changes in magnetic field during speech, a system was developed to detect words from a volunteer wearing magnets on the lips, teeth and tongue [10].

The present invention introduces a new type of artificial larynx which overcomes many of the disadvantages of the prior art devices. This new device will utilize dynamic measurement of tongue position to infer intended speech, and will transmit these signals to an electronic unit for near-real-time speech synthesis.

While a laryngectomy is by far the most common way in which humans lose their ability to speak, an accident involving the throat can crush a larynx to such an extent that a person in not able to communicate properly.

OBJECT OF THE INVENTION

It is an object of this invention to provide a means for compensating for the whole or a partial loss of speech following a a su rgical procedure, for example, a laryngectomy, or an accident.

SUMMARY OF THE INVENTION

In accordance with this invention there is provided a means for compensating for a loss of speech comprising a sensor unit capable of sensing the position of a user's tongue while endeavouring to articulate words and/or sounds, a comparator connected to the sensor unit for comparing, in use, the position of the user's tongue with a library of stored tongue positions and associated words and/or sounds, and a loudspeaker which, should a match be found between the sensed tongue positions and the stored tongue positions, projects a sound associated with the stored tongue positions.

There is also provided for the comparator to include a processor which, in use, creates words and/or sounds by selecting and, where necessary, modifying, associated words and/or sounds which are projected by the loudspeaker.

There is also provided for the position of a user's tongue to be sensed and monitored with a palatometer and a pseudopalate, preferably a Logometrix pseudopalate, the palatometer having a multiplicity of, preferably in excess of one hundred and preferably one hundred and eighteen, contact sensors which detect the position of the user's tongue relative to the palate when endeavouring to articulate words and/or sounds.

There is further provided for the position of the user's tongue relative to the palate when endeavouring to articulate words and/or sounds to be reduced to two-dimensional time-space plots which are fed into a neural network, preferably a multi-layer perception network, for analysis training and word and/or sound synthesis.

There is further provided for an output from a trained neural network to be sent to a word synthesizer to produce synthesized voice patterns or speech which, preferably, simulates a patient's original voice patterns or speech.

There is also provided for a Hidden Markov Model (HMM) to be used to anticipate words and allow for a real-time output of words.

There is further provided for suitable algorithms to be used to achieve a synthesized voice pattern as close as possible to a patient's original sound, for the algorithms to utilise, in addition to an input from the HMM, other physiological signals, preferably related to jaw movement, lip movement and inhalation and exhalation, in synthesising a patient's voice.

BRIEF DESCRIPTION OF AN EMBODIMENT OF THE INVENTION

Figure 2:
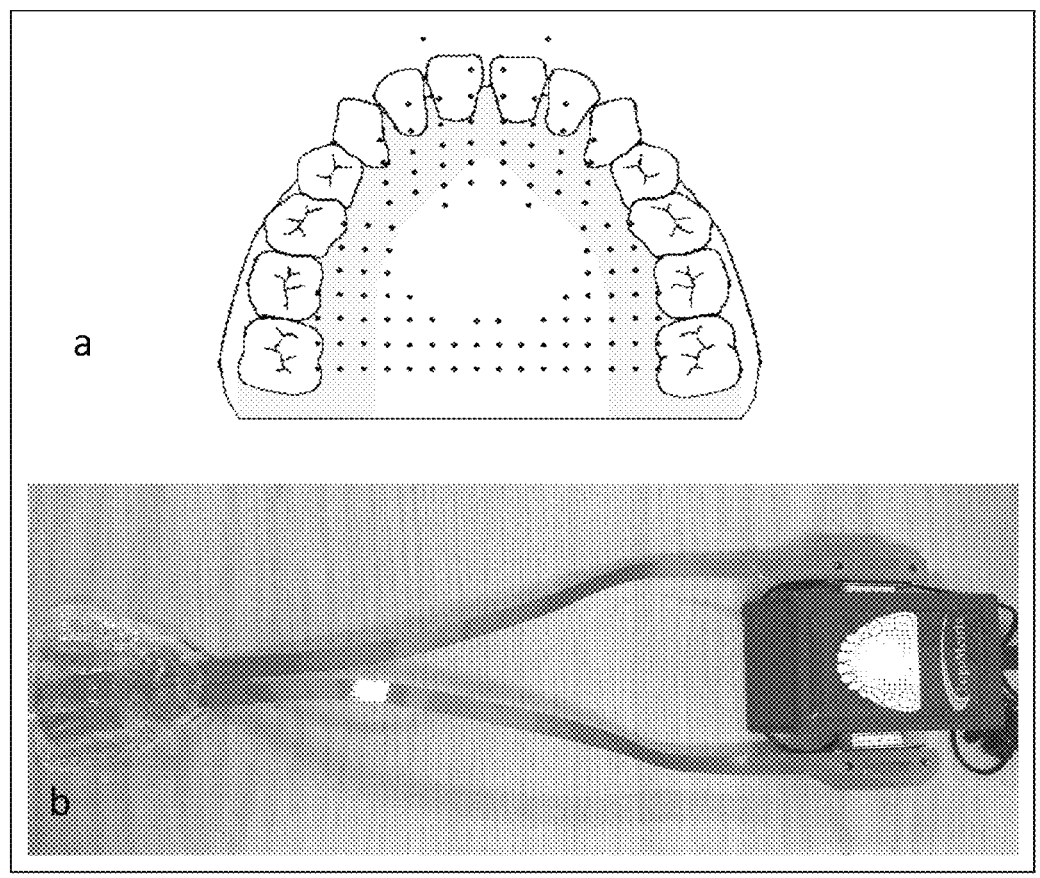
Figure 3:
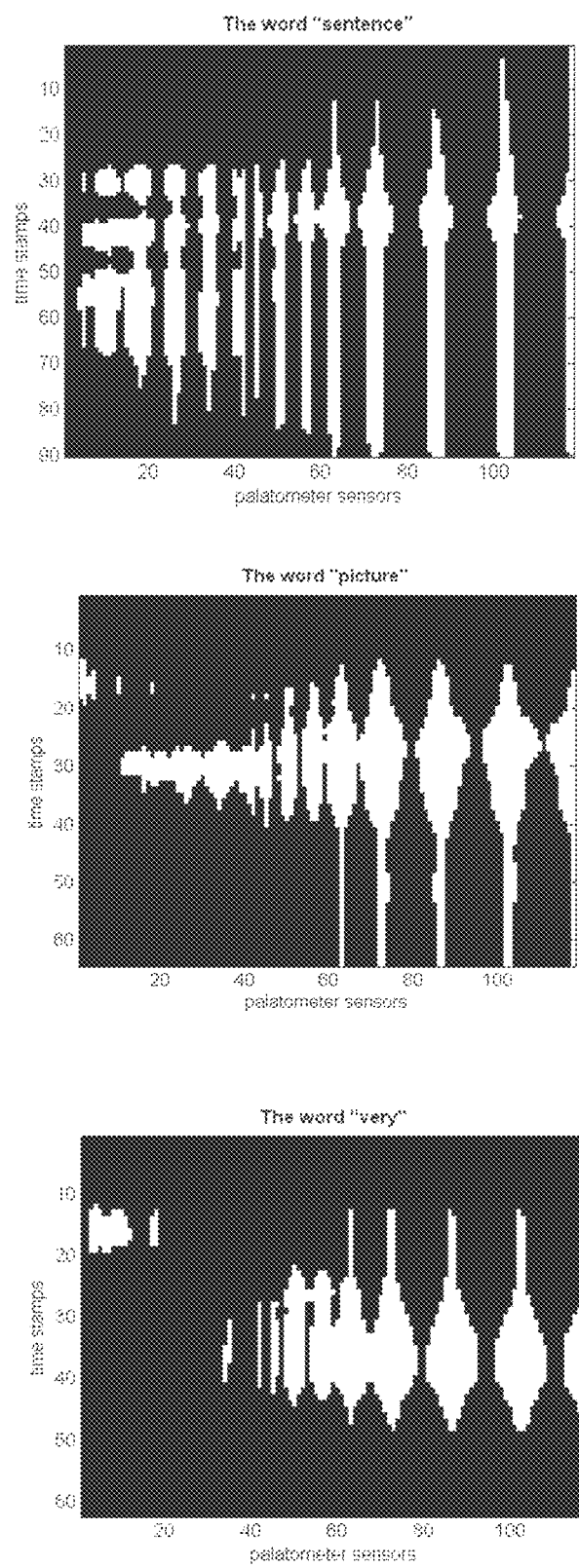
Figure 4:
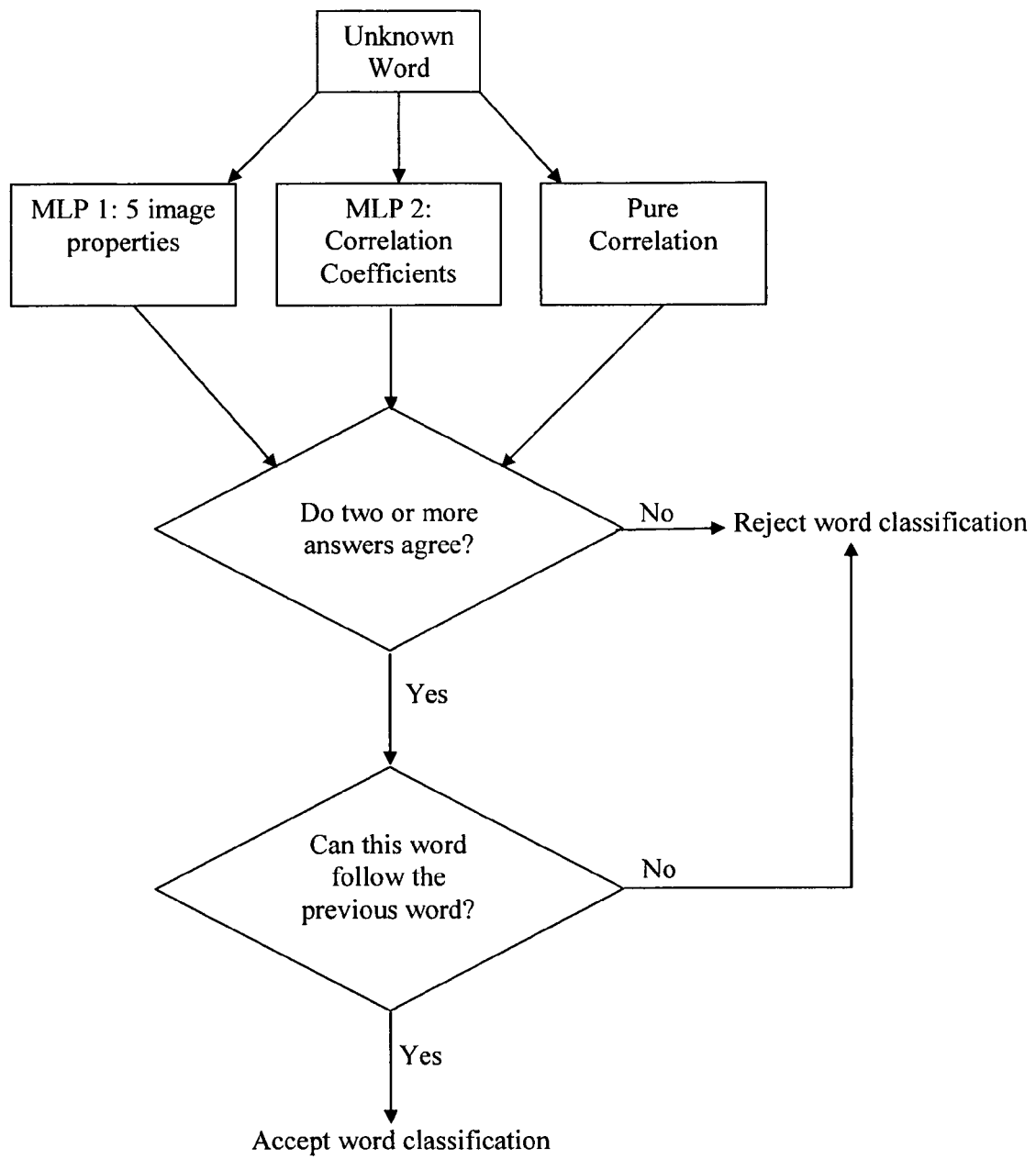

The above and additional features of the invention will be described below by way of example only and with reference to the accompanying figures in which:

FIG. 1 shows the basic anatomy of a patient after a laryngectomy taken from [11];

FIG. 2 a) is a screen shot of a Logometrix system showing placement of sensors on the LogoMetrix pseudopalate(taken from [11]); and b) illustrates the Logometrix system showing a pseudopalate and a palatometer taken from [11];

FIG. 3 is a space-time representation for the words "sentence", "picture" and "very" taken from [11]; and FIG. 4 a voting and predicting scheme for words and/or sounds

DESCRIPTION OF A PREFERRED EMBODIMENT

One embodiment of the invention will now be described by way or example only. In this embodiment a means for compensating for loss of speech, also referred to an artificial larynx, utilizes dynamic measurement of tongue position to infer intended speech and these signals are transmitted to an electronic unit for near-real-time speech synthesis. The dynamic tongue measurement is achieved with the use of a LogoMetrix Electropalatograph system consisting of a palatometer and pseudopalate (LogoMetrix, Arizona). By using a combination of data from the palatometer and from other biological signals, it is possible to infer what the patient is saying.

A. The LogoMetrix Electropalatograph (EPG) System

The LogoMetrix system uses a pseudopalate to give dynamic, real-time information about tongue-palate contact during speech. This data is collected by the pseudopalate which has 118 gold touch sensors spread over the palate (see FIG. 2). Palate data is sampled at 100 Hz. A pseudopalate is custom made for each user's mouth thus ensuring correct fit.

B. Data Representation

Data for 50 common words were recorded using the pseudopalate system. The pseudopalate contact patterns were then separated from the audio signal. These signals were then formed into a 2-D space-time plot using MATLAB (see FIG. 3). In this way, the dynamic nature of the signals is preserved and standard image processing techniques can be applied.

C. Image Recognition

Using a variety of image descriptors, unique information about the 2-D space-time images are be fed into a multi-layer perceptron (MLP) neural network [12]. This is trained to associate the various image descriptors with specific words in the vocabulary of the system.

A voting system of Multi-Layer Perceptron neural-networks (with some grammatical prediction) is shown in FIG. 4 and this system identifies the input word correctly 94.14% of the time, and has a rejection rate of 17.74% of the input words (see FIG. 4). The image descriptors used are: pure correlation, image properties (which uses image statistics such as area, Euler number, Centroid position etc) and Correlation Coefficients. In this application templates of each of the words were created by averaging a number of cases of each word together. These templates could then be correlated against an unknown word, and the template that has the highest correlation coefficient is assumed to be the closest match to the unknown word. Correlation Coefficients consist of the coefficients found by correlating each template against an unknown word.

A HMM (Hidden Markov Model) may be used in order to anticipate the words and allow for a real-time output of the words. Other artificial intelligence and pattern recognition techniques may also be considered.

D. Speech Synthesis

The outputs from the MLP and HMM will be sent to a word synthesizer. Algorithms will be included to achieve a synthesized voice pattern as close to the patient's original sound as possible. This will be done by sending other physiological signals (such as jaw opening, lip movement etc.) to the synthesizer to modulate the output. According to Menezes et al [13] the magnitude of jaw-opening corresponds to increasing syllable magnitude and emphasis. In Lim et al [14] it was shown that the fundamental frequency ($F_0$) in vowel production decreases as jaw opening increases. Inhalation and exhalation may also be used for timing. This information will all be useful in making the tone and quality of the synthesized voice as real and lifelike as possible.

Voice morphing is the process whereby the voice of a source speaker is modified so that it sounds like the voice of a target speaker. The Gaussian Mixture Model (GMM) based voice morphology method laid out in [15, 16, 17] has been implemented. With a sample of the laryngectomy-patient's pre-laryngectomy voice, the recorded words can be morphed into the patient's voice.

It is envisaged that the above described artificial larynx will be developed into a viable option for laryngectomy patients. The proposed device is novel because the speech synthesis and intended speech detection are separate, thus obviating the need to implant the sound generating part of the artificial larynx.

REFERENCES

1. Takahashi H, Nakao M, Kikuchi Y and Kaga K, "Alaryngeal speech aid using an intra-oral electrolarynx and a miniature fingertip switch", Auris Nasus Larynx, Vol. 32, 2005, pages 157-162
2. Van De Graaf, K. M, "Human Anatomy", 6$^{th}$ ed. New York: McGraw-Hill Higher Education, 2002
3. Shoureshi R. A, Chaghajerdi A, Aasted C and Meyers A, "Neural-based Prosthesis for Enhanced Voice Intelligibility in Laryngectomees", Proc. IEEE EMBS Conference on Neural Engineering, March, 2003, pages 173-176
4. Ng M. L, Kwok C. I and Chow S. W, "Speech performance of adult Cantonese-speaking laryngectomees using different types of alaryngeal phonation", Journal of Voice, Vol. 11, No. 3, 1997, pages 338-344
5. Liu H. and Ng M, L, "Electrolarynx in voice rehabilitation", Auris Nasus Larynx, 34, 2007, pages 327-332
6. P Jassar, R J A England and N D Stafford "Restoration of voice after laryngectomy", J R Svc Med, 92, 1999, pages 299-302
7. Putney FJ. "Rehabilitation of the postlaryngectomized patient." Ann Otol Rhinol Laryngol, 67, 1958 pages 544-549
8. Op de Coul BMR, Hilgers FJM, Balm AJM, Tan B, van den Hoogen FJA, van Tinteren H. "A decade of postlaryngectomy vocal rehabilitation in 318 patients. A single institution's experience with consistent application of Provox indwelling voice prostheses." Arch Otolatyngol Head Neck Surg, 126, 2000, pages 1320-1328
9. Ooe K, Fukuda T and Arai F, "A New Type of Artificial Larynx Using a PZT Ceramics Vibrator as a Sound Source", IEEE/ASME Transactions on Mechatronics, Vol. 5, No. 2, June 2000
10. Fagan MJ, Ell SR, Gilbert JM, Sarrazin E and Chapman PM, "Development of a (silent) speech recognition system for patients following laryngectomy", Med Eng Phys, 2007, in press
11. M J Russell, D M Rubin, B Widorowitz and T Marwala, "The Artificial Larynx: A Review of Current Technology and a Proposal for Future Development", NBC 2008, Proceedings Vol. 20, pp. 160-163, June 2008
12. M J Russell, D M Rubin, T Marwala and B Wigdorowitz, "Pattern Recognition and Feature Selection for the Development of a New Artificial Larynx", Proceedings of The World Congress Of Biomedical Engineering and Medical Physics, Munich, September, 2009, in press
13. Menezes C., Erickson D. and Fujimura O, "Contrastive Emphasis: Comparison of Pitch Accents with Syllable Magnitudes", Proc. Of Speech Prosody, France, April, 2002
14. Lim M, Lin E. and Bones P, "Vowel Effect on Glottal Parameters and the Magnitude of Jaw Opening", Journal of Voice, Vol. 20, No. 1, 2006, pages 46-54
15. H. Duxans, D. Erro, J. Pérez, F. Diego, A. Bonafonte, A. Moreno "Voice Conversion of Non-Aligned Data using Unit Selection", TC-Star Workshop on Speech to Speech Translation. Barcelona, Spain. June 2006.
16. D. Erro, A. Moreno "Weighted Frequency Warping for Voice Conversion" InterSpeech 2007- EuroSpeech. Antwerp, Belgium. August 2007
17. D. Erro, A. Moreno "Frame Alignment Method for Cross-lingual Voice Conversion" InterSpeech 2007 - EuroSpeech. Antwerp, Belgium. August 2007

The invention claimed is:

1. An apparatus for compensating for a loss of speech, comprising:
    a sensor unit wherein the sensor unit senses the position of a user's tongue while the user articulates words or sounds;
    a comparator connected to the sensor unit wherein the comparator compares the position of the user's tongue with a library of stored tongue positions and associated words or sounds, the comparator including a processor which creates words or sounds by selecting and, where necessary, modifying, associated words or sounds for projection by a loudspeaker; and
    a loudspeaker being coupled with the processor wherein when a match is found between the sensed tongue positions and the stored tongue positions, the loudspeaker then projects a sound associated with the stored tongue positions.

2. The apparatus of claim 1, wherein the sensor unit includes a palatometer and a pseudopalate for sensing, in use, the position of the user's tongue.

3. The apparatus of claim 2, wherein the pseudopalate is a Logometrix pseudopalate.

4. The apparatus of claim 2, wherein the palatometer has a multiplicity of contact sensors which detect the position of the user's tongue relative to the user's palate when endeavouring to articulate words or sounds.

5. The apparatus of claim 4, wherein the palatometer has in excess of one hundred contact sensors.

6. The apparatus of claim 5, wherein the palatometer has one hundred and eighteen contact sensors.

7. The apparatus of claim 1, wherein the position of the user's tongue relative to the user's palate when the user articulates words or sounds is reduced to two-dimensional time-space plots which are fed into a neural network for analysis training and word or sound synthesis.

8. The apparatus of claim 7, wherein the neural network is a multi-layer perception network.

9. The apparatus of claim 7, wherein an output from the neural network is sent to a word synthesizer to produce synthesized voice patterns or speech.

10. The apparatus of claim 9, wherein the synthesized voice patterns or speech simulate the user's original voice patterns or speech.

11. The apparatus of claim 1, wherein a Hidden Markov Model (HMM) is used to anticipate words and allow for a real-time output of words.

12. The apparatus of claim 1, wherein suitable algorithms are used to achieve a synthesized voice pattern as close as possible to the user's original sound.

13. The apparatus of claim 12, wherein the algorithms utilise, in addition to an input from the HMM, other physiological signals to synthesise the user's voice.

14. The apparatus of claim 13, wherein the other physiological signals are related to jaw movement, lip movement and inhalation and exhalation.

15. The apparatus of claim 2, wherein the position of the user's tongue relative to the user's palate when the user articulates words or sounds is reduced to two-dimensional time-space plots which are fed into a neural network for analysis training and word or sound synthesis.

16. The apparatus of claim 3, wherein the palatometer has a multiplicity of contact sensors which detect the position of the user's tongue relative to the user's palate when endeavouring to articulate words or sounds.

17. The apparatus of claim 7, wherein a Hidden Markov Model (HMM) is used to anticipate words and allow for a real-time output of words.

18. The apparatus of claim 9, wherein suitable algorithms are used to achieve a synthesized voice pattern as close as possible to the user's original sound.

* * * * *